United States Patent [19]

Temperilli et al.

[11] 4,317,912
[45] Mar. 2, 1982

[54] TETRACYCLIC INDOLE DERIVATIVES

[75] Inventors: Aldemio Temperilli; Sergio Mantegani; Giuliana Arcari; Anna M. Caravaggi, all of Milan, Italy

[73] Assignee: Farmitalia Carlo Erba S.p.A., Milan, Italy

[21] Appl. No.: 129,333

[22] Filed: Mar. 11, 1980

[30] Foreign Application Priority Data

Mar. 16, 1979 [GB] United Kingdom ............... 09281/79

[51] Int. Cl.³ .................. A61K 31/40; A61K 31/445; A61K 31/535; C07D 487/00
[52] U.S. Cl. .................................. 546/199; 544/142; 424/248.54; 424/248.57; 424/267; 424/274; 260/326.25; 260/326.62; 260/326.5 B; 260/326.85
[58] Field of Search ...................... 260/326.25, 326.62, 260/326.5 B, 326.85; 546/199; 544/142; 424/274, 267, 248.54, 248.57

[56] References Cited

U.S. PATENT DOCUMENTS 3,393,208  7/1968  Plostnieks ..................... 260/326.5 B
3,397,202  8/1968  Plostnieks ..................... 260/326.25

FOREIGN PATENT DOCUMENTS 1482871  8/1977  United Kingdom ........... 260/326.25

Primary Examiner—Alton D. Rollins
Attorney, Agent, or Firm—Stevens, Davis, Miller & Mosher

[57] ABSTRACT pg,1 A compound is disclosed of the formula (I):

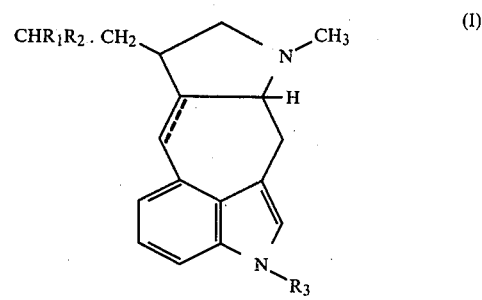

wherein $R_1$ represents a hydrogen atom, or a carboxy, alkoxycarbonyl, piperidinocarbonyl, 1-pyrrolidinylcarbonyl, morpholinocarbonyl, carbamoyl or benzylcarbamoyl group, or an alkylcarbamoyl or dialkylcarbamoyl group in which the, or each, alkyl group has from 1 to 4 carbon atoms;

$R_2$ represents a hydrogen or fluorine atom, or a cyano, acetyl or carbamoyl group; and $R_3$ represents a hydrogen atom or a methyl group; and represents a single or a double bond, with the proviso that $R_1$ and $R_2$ do not simultaneously represent hydrogen atoms;

or a pharmaceutically acceptable salt thereof.

24 Claims, No Drawings

TETRACYCLIC INDOLE DERIVATIVES

This invention relates to 5(10→9)abeo-ergoline derivatives and to processes for their preparation.

The invention provides 5(10→9)abeo-ergoline derivatives of the general formula (I):

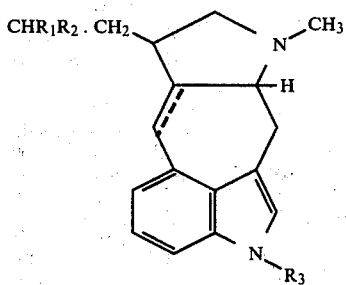

wherein
- $R_1$ represents a hydrogen atom, or a carboxy, alkoxycarbonyl, piperidinocarbonyl, 1-pyrrolidinylcarbonyl, morpholinocarbonyl, carbamoyl or benzylcarbamoyl group, or an alkylcarbamoyl or dialkylcarbamoyl group in which the, or each, alkyl group has from 1 to 4 carbon atoms;
- $R_2$ represents a hydrogen or fluorine atom, or a cyano, acetyl or carbamoyl group; and
- $R_3$ represents a hydrogen atom or a methyl group; and
- ----- represents a single or a double bond, and with the proviso that $R_1$ and $R_2$ do not simultaneously represent hydrogen atoms.

This invention further provides a process for the preparation of 5(10→9)abeo-ergoline derivatives of the general formula (I) where $R_1$ represents an ethoxycarbonyl group, ----- represents a double bond, and $R_2$ and $R_3$ are as above defined, the process comprising condensing a 5(10→9)abeo-9,10-didehydro-6-methyl-ergoline-8β-methanol tosylate of the general formula (II) hereinbelow, wherein $R_3$ is as above defined, with a compound of the formula $CH_2R_2 \cdot COOC_2H_5$, wherein $R_2$ is as above defined, the condensation being effected in a polar aprotic solvent at a temperature of from 50° C. to 100° C. for 2 to 10 hours.

The process is schematically illustrated below:

Suitable polar aprotic solvents include dimethylsulphoxide and dimethylformamide.

The compounds (II) are known compounds, and are described in British Pat. No. 1,482,871.

The compounds (I) wherein ----- represents a double bond, other than compounds (III), may be prepared from compounds (III) by hydrolysis (to give compounds in which $R_1$ represents a carboxy group), hydrolysis and esterification with an alkanol other than ethanol (to give compounds in which $R_1$ represents an alkoxycarbonyl group other than ethoxycarbonyl), hydrolysis and decarboxylation (to give compounds in which $R_1$ represents a hydrogen atom), or by treatment with ammonia, benzylamine, piperidine, pyrrolidine or morpholine, or an alkylamine or a dialkylamine in which the, or each, alkyl group has from 1 to 4 carbon atoms (to give compounds in which $R_1$ represents a carbamoyl, benzylcarbamoyl, piperidinocarbonyl, 1-pyrrolidinylcarbonyl or morpholinocarbonyl group, or an alkylcarbamoyl or dialkylcarbamoyl group in which the, or each, alkyl group has from 1 to 4 carbon atoms).

Alternatively, compounds (III) in which $R_2$ is cyano can be hydrolyzed and decarboxylated to give a propionitrile which, by esterification and treatment with ammonia, benzylamine, piperidine, pyrrolidine or morpholine, or an alkylamine or a dialkylamine in which the, or each, alkyl group has from 1 to 4 carbon atoms, may be converted into compounds (I) in which $R_2$ is a hydrogen atom and $R_1$ represents a carbamoyl, benzylcarbamoyl, piperidinocarbonyl, 1-pyrrolidinylcarbonyl or morpholinocarbonyl group, or an alkylcarbamoyl or dialkylcarbamoyl group in which the, or each, alkyl group has from 1 to 4 carbon atoms.

These functional group interconversions may be effected under conditions per se well known to those skilled in the art.

The compounds (I) wherein ----- represents a single bond may be prepared from the corresponding compounds (I) wherein ----- represents a double bond by hydrogenation, using a palladium/carbon catalyst.

The cis-trans forms may be separated by conventional methods, for example by conversion into oxalate salts and fractional crystallization thereof, and alkaline treatment of the products.

The compounds (I) and their pharmaceutically acceptable acid addition salts are useful antihypertensive agents, devoid of emetic activity, and with low toxicity, and can be administered orally or parenterally in admix-

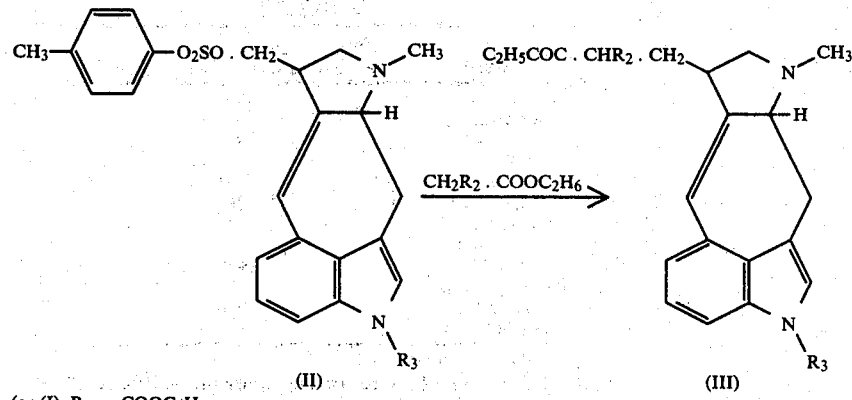

(or (I): $R_1 = COOC_2H_5$,

----- is a double bond)

ture with a suitable vehicle of an otherwise conventional nature.

EVALUATION OF ANTI-HYPERTENSIVE ACTIVITY

1. Spontaneously Hypertensive Rat (MHS):

Four spontaneously hypertensive male rats, strains MHS, weighing 250–300 g for each group were used.

The animals were treated for four consecutive days. Drugs were administered by gastric gavage, suspended in 5% arabic gum (0.2 ml/100 g body weight). Blood pressure (BP) and heart rate (HR) were measured at the tail by BP Recorder W+W. Blood pressure and heart rate were measured on the 1st and 4th day of treatment, 1 hour before and 1 and 5 hours after drug administration. The results are reported in Tables 1 and 2 below.

2. Spontaneously Hypertensive Rat (Okamoto):

Blood pressure recordings were made in conscious hypertensive unrestrained rats weighing approximately 300 g, via a catheter cronically inserted into the left common carotid artery. Implantation of arterial cannula was made under sodium pentobarbital anesthesia (50 mg/kg i.p.). A 1 cm long incision was made through the previously shaved ventral surface of the neck and the tissues overlying the trachea parted by blunt dissection to reveal the carotid artery. The polyethylene catheter used was made with PE 50 tubing, previously filled with saline containing 250 I.U./ml heparin. The tip of the cannula was pushed at least 2 cm inside the vessel toward the heart. The cannula was then firmly tied and passed beneath the skin to emerge from a small incision in the back of the neck. During the postoperative period and before the start of each recording session, the cannula was flushed through daily with saline containing heparin (250 U.I./ml). The experiments were performed two days after surgery. Drugs were administered by gastric gavage. Results are reported in Tables 3 and 4 below.

EVALUATION OF THE TOXICITY

The male mice for each group were orally treated with drugs at different dose levels for the determination of orientative toxicity. The mice were observed for seven days after administration.

The data obtained are summarized in Table 5 below.

TABLE 1

Variation in blood pressure (BP) in MHS rats. The values represent the mean obtained in 4 animals.

| Compound | Dose mg/kg os | 1st day | | 4th day | |
|---|---|---|---|---|---|
| | | Change in BP (mmHg) | | | |
| | | 1 hr after dose | 5 hrs after dose | 1 hr after dose | 5 hrs after dose |
| 355/1165 | 0.5 | −13 | −17 | −17 | −3 |
| (EXAMPLE 8) | 1 | −15 | −19 | −30 | −42 |
| | 2 | −25 | −53 | −33 | −45 |
| 355/1166 | 5 | −8 | −20 | −22 | −26 |
| (EXAMPLE 9) | | | | | |
| Hydralazine | 1 | 0 | −10 | +7 | +2 |
| | 3 | −43 | −29 | −15 | +5 |
| α-Methyl-DOPA | 30 | −27 | −4 | −2 | 0 |
| | 100 | −6 | −22 | −19 | −31 |
| 355/1225 | 1 | −28 | −17 | −34 | −21 |
| (EXAMPLE 13) | 5 | −67 | −42 | −34 | −21 |
| 355/1226 | 1 | −32 | −27 | −21 | −42 |
| (EXAMPLE 14) | 3 | −47 | −57 | −40 | −42 |
| 355/1229 | 1 | −26 | −19 | −21 | −12 |
| (EXAMPLE 2) | 5 | −26 | −20 | −36 | −45 |

TABLE 2

Variation in heart rate (HR) in MHS rats. The values represent the mean obtained in 4 animals.

| Compound | Dose mg/kg os | 1st day | | 4th day | |
|---|---|---|---|---|---|
| | | Change in HR (b/min) | | | |
| | | 1 hr after dose | 5 hrs after dose | 1 hr after dose | 5 hrs after dose |
| 355/1165 | 0.5 | −25 | −25 | −30 | −35 |
| (EXAMPLE 8) | 1 | −20 | −15 | −27 | −20 |
| | 2 | −47 | −80 | −48 | −55 |
| 355/1166 | 5 | −25 | −25 | −35 | −20 |
| (EXAMPLE 9) | | | | | |
| Hydralazine | 1 | +20 | +25 | +30 | +15 |
| | 3 | +31 | +34 | +18 | +13 |
| α-Methyl-DOPA | 30 | +33 | +36 | +50 | +20 |
| | 100 | +73 | +40 | +70 | +20 |
| 355/1225 | 1 | +5 | −22 | −40 | −43 |
| (EXAMPLE 13) | 5 | −32 | −4 | −55 | −59 |
| 355/1226 | 1 | −20 | +3 | −5 | −13 |
| (EXAMPLE 14) | 3 | −20 | −10 | −40 | −45 |
| 355/1229 | 1 | +25 | −2 | −18 | −53 |
| (EXAMPLE 2) | 5 | −40 | −35 | −50 | −55 |

TABLE 3

Variation in blood pressure in hypertensive rats (Okamoto). The values represent the mean obtained in 6 animals.

| Compound | Dose mg/kg os | Change (mmHg) in blood pressure after treatment | | | | |
|---|---|---|---|---|---|---|
| | | 30' | 60' | 120' | 240' | 360' |
| 355/1165 (EXAMPLE 8) | 1 | −21 | −29 | −33 | −26 | −23 |
| 355/1166 (EXAMPLE 9) | 5 | 0 | −3 | −15 | −18 | −10 |
| Hydralazine | 3 | −25 | −33 | −40 | −29 | −7 |
| 355/1226 (EXAMPLE 14) | 3 | −19 | −28 | −40 | −32 | −25 |

TABLE 4

Variation in heart rate in hypertensive rats (Okamoto). The values represent the mean obtained in 6 animals.

| Compound | Dose mg/kg os | Change (b/min) in heart rate after treatment | | | | |
|---|---|---|---|---|---|---|
| | | 30' | 60' | 120' | 240' | 360' |
| 355/1165 (EXAMPLE 8) | 1 | −25 | −45 | −52 | −8 | +18 |
| 366/1166 (EXAMPLE 9) | 5 | −20 | −20 | −35 | −15 | −20 |
| Hydralazine | 3 | +50 | +21 | +52 | +3 | +3 |
| 355/1226 (EXAMPLE 14) | 3 | −33 | −30 | −23 | −16 | +4 |

TABLE 5

Acute toxicity.

| Compound | Orientative toxicity in mice (mg/kg per os) |
|---|---|
| 355/1165 (EXAMPLE 8) | >1000 |
| 355/1166 (EXAMPLE 9) | >800 |
| Hydralazine* | 122 |
| α-Methyl-DOPA* | 5300 |
| 355/1225 (EXAMPLE 13) | 600 |
| 355/1226 (EXAMPLE 14) | >800 |
| 355/1229 (EXAMPLE 2) | 600 |

*Data of LD$_{50}$ from the literature.

In Tables 1 and 2 are reported the results of the study of the activity of compounds 355/1165 and 355/1166 upon the BP and HR (measured indirectly by means of a tail cuff) of spontaneous hypertensive rats, MHS strain (4 rats each group). The compounds were given orally, once a day for 4 consecutive days.

Compound 355/1165 at the doses tested of 0.5, 1 and 2 mg/kg per os, significantly lowers BP on the 1st and 4th day after the treatment. This effect is correlated to the dose administered and lasting until the 5th hour postdosings.

The compound 355/1166 at 5 mg/kg per os lowers BP at each recording session, but its effect is more pronounced after the 4th dose.

The compound 355/1225 orally given at doses of 1 and 5 mg/kg reduces blood pressure in dose-dependent manner on both the 1st and 4th day of treatment. The peak effect is reached one hour after dosing.

The compound 355/1226 at both the doses tried (1 and 3 mg/kg per os) decreases BP; especially with the higher dose, this effect is remarkable and long lasting.

The compound 355/1229 was tried at doses of 1 and 5 mg/kg per os; both dosages reduce BP in a similar way on the 1st day, when during the 4th day the decrease of BP is dose-dependent.

Compound 355/1165 at 2 mg/kg per os and compound 355/1226 at 3 mg/kg per os show a more marked antihypertensive activity on the 1st day compared with Hydralazine (3 mg/kg per os) and even greater effect on the 4th day, because with compound 355/1165 and compound 355/1226 tolerance does not occur after repeated administration. Compared with α-methyl-DOPA, the two compounds are 50 times more active.

The compound 355/1166 at the dose tested of 5 mg/kg per os, proved to be 20 times more effective than α-methyl-DOPA. This compound has a less pronounced activity than Hydralazine (3 mg/kg per os) on the 1st day; its effect, moreover, is longer lasting, because 1st and 5th hours after the 4th administration, compound 355/1166 shows a greater hypotensive effect.

The compounds 355/1225 and 355/1229 at the dose of 5 mg/kg per os, show a greater activity during both the 1st and 4th day of treatment than Hydralazine (3 mg/kg per os) and α-methyl-DOPA. No tolerance occurs with these compounds.

Bradycardia is observed at all the doses treated; hydralazine and α-methyl-DOPA show no effect on heart rate (Table 2).

Tables 3 and 4 summarize the oral activity of compounds 355/1165, 355/1166 and 355/1226 on BP and HR of spontaneous hypertensive rats (SHR, Okamoto strain) provided with cronic cannulation of the left carotid artery. Using this strain of hypertensive rats compound 355/1165 (1 mg/kg per os) is 3 times more active than hydralazine and shows a marked and long lasting hypotensive activity, whereas compound 355/1166 (5 mg/kg per os) is less effective than the reference compound.

Compound 355/1226 (3 mg/kg per os) shows an intermediate activity between compound 355/1165 and compound 355/1166.

Changes on HR taking place after the administration of compounds 355/1165, 355/1166 and 355/1226 are reported in Table 4. It should be noted that in any case these compounds produce a slight bradycardia and never tachicardia.

The results of preliminary oral toxicity tests show that all compounds are less toxic than hydralazine and have a higher therapeutic index than α-methyl-DOPA.

The following examples still further illustrate the invention:

EXAMPLE 1

2-Cyano-3-[5(10→9)abeo-9,10-didehydro-6-methylergoline-8β]-propionic acid ethyl ester. (III: $R_3$=H)

A mixture of 4.65 g of sodium ethyl cyanoacetate, 7 g of 5(10→9)abeo-9,10-didehydro-6-methyl-ergoline-8β-methanol tosylate and 2.8 g of potassium iodide in 100 ml of dimethylsulphoxide and 1 ml of ethyl cyanoacetate was heated under stirring at 70° C. for 5 hours. The solution was poured into 500 ml of iced water. The resultant precipitate was filtered off, dried and chromatographed on a silica gel column using chloroform as eluant, giving 3.5 g of the title compound, m.p. 191°–193° C.

EXAMPLE 2

2-Cyano-3-[5(10→9)abeo-9,10-didehydro-6-methyl-ergoline-8β]-propionamide. (355/1229). (I: $R_1$=NH$_2$CO, $R_2$=CN, $R_3$=H, ⎓⎓⎓ is a double bond)

2 g of 2-cyano-3-[5(10→9)abeo-9,10-didehydri-6-methylergoline-8β]-propionic acid ethyl ester, prepared as described in Example 1, were dissolved in 100 ml of methanol saturated with liquid ammonia. The solution was kept in a stoppered vessel at room temperature for 2 hours, and then evaporated to dryness to give 1.4 g of the title compound, m.p. 184°–186° C.

EXAMPLE 3

2-Cyano-3-[5(10→9)abeo-9,10-didehydro-6-methyl-ergoline-8β]-N-ethylpropionamide. (I: $R_1$=C$_2$H$_5$NHCO, $R_2$=CN, $R_3$=H, ⎓⎓⎓ is a double bond)

Operating as in Example 2, but employing ethylamine instead of ammonia, the title compound was obtained as a foam in 70% yield.

EXAMPLE 4

2-Cyano-3-[5(10→9)abeo-9,10-didehydro-6-methyl-ergoline-8β]-N-benzyl-propionamide. (I: $R_1$=C$_6$H$_5$CH$_2$NHCO, $R_2$=CN, $R_3$=H, ⎓⎓⎓ is a double bond)

Operating as in Example 2, but employing benzylamine instead of ammonia, the title compound was obtained as a foam in 60% yield.

EXAMPLE 5

2-Cyano-3-[5(10→9)abeo-9,10-didehydro-6-methyl-ergoline-8β]-N-propionylpyrrolidine. (I: $R_1$=1-pyrrolidinyl-carbonyl, $R_2$=CN, $R_3$=H, ⎓⎓⎓ is a double bond)

Operating as in Example 2, but employing pyrrolidine instead of ammonia, the title compound was obtained as a foam in 65% yield.

EXAMPLE 6

5(10→9)abeo-9,10-didehydro-6-methyl-ergoline-8β-propionitrile. (I: $R_1$=$R_3$=H, $R_2$=CN, ⎓⎓⎓ is a double bond)

1.2 g of 2-cyano-3-[5(10→9)abeo-9,10-didehydro-6-methyl-ergoline-8β]-propionic acid ethyl ester, prepared as described in Example 1, were dissolved in 50 ml of methanol and treated with 0.5 g of sodium hydroxide in 20 ml of water. After stirring for 3 hours, the solution was poured into water and neutralized with dilute acetic acid. The 2-cyano-3-[5(10→9)abeo-9,10- didehydro-6-methyl-ergoline-8β]-propionic acid was filtered off and dissolved in 30 ml of dimethylformamide. It was then warmed at 120° C. for 24 hours to effect decarboxylation. After evaporation off of the solvent, the title compound was obtained as a foam in 80% yield.

EXAMPLE 7

5(10→9)abeo-9,10-didehydro-6-methyl-ergoline-8β-propionamide. (I: $R_1=R_3=H$, $R_2=CONH_2$, ⁓⁓ is a double bond)

0.7 g of 5(10→9)abeo-9,10-didehydro-6-methyl-ergoline-8β-propionitrile, prepared as described in Example 6, was dissolved in 50 ml of t-butanol and treated with 1 g of potassium hydroxide. The mixture was refluxed for 24 hours. After evaporating off the solvent, the title compound was obtained as a foam in 69% yield.

EXAMPLE 8

2-Cyano-3-[trans-5(10→9)abeo-6-methyl-ergoline-8β]-propionamide (355/1165). (I: $R_1=NH_2CO$, $R_2=CN$, $R_3=H$, ⁓⁓ is a single bond)

A solution of 2.5 g of 2-cyano-3-[5(10→9)abeo-9,10-didehydro-6-methyl-ergoline-8β]-propionamide, prepared as described in Example 2, in 500 ml of ethanol was hydrogenated in the presence of 4 g of a 10% palladium on carbon catalyst. After evaporating off the ethanol, the residue was treated with one mole of oxalic acid and the salts of the cis and trans forms were separated by fractional crystallization from water in which the oxalate of the trans form is less soluble. Treatment of the trans-oxalate with potassium hydroxide gave 1 g of the title compound, m.p. 251°-252° C.

EXAMPLE 9

2-Cyano-3-[trans-5(10→9)abeo-6-methyl-ergoline-8β]-propionic acid ethyl ester (355/1166). (I: $R_1=COOC_2H_5$, $R_2=CN$, $R_3=H$, ⁓⁓ is a single bond)

Operating as in Example 8, but employing 2-cyano-3-[5(10→9)abeo-9,10-didehydro-6-methyl-ergoline-8β]-propionic acid ethyl ester, prepared as described in Example 1, the title compound was obtained in 40% yield, m.p. 182°-184° C.

EXAMPLE 10

2-Cyano-3-[trans-5(10→9)abeo-6-methyl-ergoline-8β]-N-ethylpropionamide. (I: $R_1=C_2H_5NHCO$, $R_2=CN$, $R_3=H$, ⁓⁓ is a single bond)

Operating as in Example 8, but employing 2-cyano-3-[5(10→9)abeo-9,10-didehydro-6-methyl-ergoline-8β]-N-ethylpropionamide, prepared as described in Example 3, the title compound was obtained as a foam in 40% yield.

EXAMPLE 11

2-Cyano-3-[trans-5(10→9)abeo-6-methyl-ergoline-8β]-N-benzylpropionamide. (I: $R_1=C_6H_5CH_2.NHCO$, $R_2=CN$, $R_3=H$, ⁓⁓ is a single bond)

Operating as in Example 8, but employing 2-cyano-3-[5(10→9)abeo-9,10-didehydro-6-methyl-ergoline-8β]-N-benzylpropionamide, prepared as described in Example 4, the title compound was obtained as a foam in 35% yield.

EXAMPLE 12

2-Cyano-3-[trans-5(10→9)abeo-6-methyl-ergoline-8β]-propionylpyrrolidine. (I: $R_1=$ 1-pyrrolidinylcarbonyl, $R_2=CN$, $R_3=H$, ⁓⁓ is a single bond)

Operating as in Example 8, but employing 2-cyano-3-[5(10→9)abeo-9,10-didehydro-6-methyl-ergoline-8β]-propionylpyrrolidine, prepared as described in Example 5, the title compound was obtained as a foam in 40% yield.

EXAMPLE 13

Trans-5(10→9)abeo-6-methyl-ergoline-8β-propionitrile. (355/1225) (I: $R_1=R_3=H$, $R_2=CN$, ⁓⁓ is a single bond)

Operating as in Example 8, but employing 5(10→9)abeo-9,10-didehydro-6-methyl-ergoline-8β-propionitrile, prepared as described in Example 6, the title compound was obtained in 50% yield, m.p. 167°-169° C.

EXAMPLE 14

Trans-5(10→9)abeo-6-methyl-ergoline-8β-propionamide. (I: $R_1=R_3=H$, $R_2=CONH_2$, ⁓⁓ is a single bond) (355/1226)

Operating as in Example 8, but employing 5(10→9)abeo-9,10-didehydro-6-methyl-ergoline-8β-propionamide, prepared as described in Example 7, the title compound was obtained in 45% yield, m.p. 205°-207° C.

EXAMPLE 15

Trans-5(10→9)abeo-6-methyl-ergoline-8β-N-ethyl-propionamide 2 g of trans-5(10→9)abeo-6-methyl-ergoline-8β-propionitrile, prepared as described in Example 13, in 20 ml of dioxane, 10 ml of ethanol, and 10 ml of 30% KOH were refluxed for 18 hours.

The solution was evaporated in vacuo and the residue was suspended in 60 ml of methanol containing 6 ml of $H_2SO_4$. After 4 hours at room temperature the solution was diluted with water, basified with $NH_4OH$, and extracted with chloroform. Evaporation of the solvent left a residue of trans-5(10→9)abeo-6-methyl-ergoline-8β-propionic acid methyl ester (m.p. 203°-205° C.) that was dissolved in 50 ml of methanol and 2 ml of ethylamine. The solution was kept in a Parr bomb at 100° C. for 3 days, then the solution was evaporated to give 1.5 g of the title compound, m.p. 227°-229° C.

EXAMPLE 16

Trans-5(10→9)abeo-6-methyl-ergoline-8β-N-benzylpropionamide

Operating as in Example 15, but employing benzylamine, the title compound was obtained, m.p. 185°-187° C., in 60% yield.

EXAMPLE 17

Trans-5(10→9)abeo-6-methyl-ergoline-8β-N-propionylpyrrolidine

Operating as in Example 15, but employing pyrrolidine, the title compound m.p. 202°-204° C., was obtained in 55% yield.

EXAMPLE 18

Trans-5(10→9)abeo-6-methyl-ergoline-8β-N-propionylpiperidine

Operating as in Example 15, but employing piperidine, the title compound was obtained as a foam in 50% yield.

EXAMPLE 19

Trans-5(10→9)abeo-6-methyl-ergoline-8β-N-allyl-propionamide

Operating as in Example 15, but employing allylamine, the title compound was obtained as a foam in 40% yield.

EXAMPLE 20

Trans-5(10→9)abeo-6-methyl-ergoline-8β-N-n.butyl-propionamide

Operating as in Example 15, but employing n.butylamine, the title compound was obtained as a foam in 65% yield.

EXAMPLE 21

Trans-5(10→9)abeo-6-methyl-ergoline-8β-N-diethyl-propionamide

Operating as in Example 15, but employing diethylamine, the title compound was obtained as a foam in 50% yield.

EXAMPLE 22

Trans-5(10→9)abeo-6-methyl-ergoline-8β-N-i.propyl-propionamide

Operating as in Example 15, but employing isopropylamine, the title compound was obtained as a foam in 60% yield.

EXAMPLE 23

Trans-5(10→9)abeo-6-methyl-ergoline-8β-N-methylbutylpropionamide

Operating as in Example 15, but employing N-methylbutylamine, the title compound was obtained as a foam in 75% yield.

What is claimed is:

1. A compound of the formula (I):

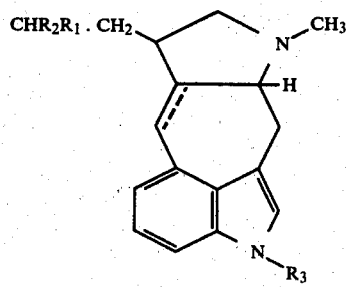

wherein $R_1$ represents a hydrogen atom, or a carboxy, alkoxycarbonyl, piperidinocarbonyl, 1-pyrrolidinylcarbonyl, morpholinocarbonyl, carbamoyl or benzylcarbamoyl group, or an alkylcarbamoyl or dialkylcarbamoyl group in which the, or each, alkyl group has from 1 to 4 carbon atoms;

$R_2$ represents a hydrogen or fluorine atom, or a cyano, acetyl or carbamoyl group; and $R_3$ represents a hydrogen atom or a methyl group; and $\overline{\phantom{--------}}$ represents a single or a double bond, with the provisos that $R_1$ and $R_2$ do not simultaneously represent hydrogen atoms, when $R_1$ is hydrogen, $R_2$ is acetyl and when $R_2$ is hydrogen $R_1$ is not hydrogen, carboxy, alkoxycarbonyl, or carbamoyl;

or a pharmaceutically acceptable salt thereof.

2. 2-cyano-3-[5(10→9)abeo-9,10-didehydro-6-methyl-ergoline-8β]-propionic acid ethyl ester.

3. 2-cyano-3-[5(10→9)abeo-9,10-didehydro-6-methyl-ergoline-8β]-propionamide.

4. 2-cyano-3-[5(10→9)abeo-9,10-didehydro-6-methyl-ergoline-8β]-N-ethylpropionamide.

5. 2-cyano-3-[5(10→9)abeo-9,10-didehydro-6-methyl-ergoline-8β]-N-benzylpropionamide.

6. 2-cyano-3-[5(10→9)abeo-9,10-didehydro-6-methyl-ergoline-8β]-N-propionylpyrrolidine.

7. 2-cyano-3-[trans-5(10→9)abeo-6-methyl-ergoline-8β]-propionamide.

8. 2-cyano-3-[trans-5-(10→9)abeo-6-methyl-ergoline-8β]-propionic acid ethyl ester.

9. 2-cyano-3-[trans-5(10→9)abeo-6-methyl-ergoline-8β]-N-ethylpropionamide.

10. 2-cyano-3-[trans-5(10→9)abeo-6-methyl-ergoline-8β]-N-benzylpropionamide.

11. 2-cyano-3-[trans-5(10→9)abeo-6-methyl-ergoline-8β]-propionylpyrrolidine.

12. Trans-5(10→9)abeo-6-methyl-ergoline-8β-propionitrile.

13. Trans-5(10→9)abeo-6-methyl-ergoline-8β-propionamide.

14. Trans-5(10→9)abeo-6-methyl-ergoline-8β-N-ethyl-propionamide.

15. Trans-5(10→9)abeo-6-methyl-ergoline-8β-N-benzyl-propionamide.

16. Trans-5(10→9)abeo-6-methyl-ergoline-8β-N-propionylpyrrolidine.

17. Trans-5(10→9)abeo-6-methyl-ergoline-8β-N-propionylpiperidine.

18. Trans-5(10→9)abeo-6-methyl-ergoline-8β-N-allyl-propionamide.

19. Trans-5(10→9)abeo-6-methyl-ergoline-8β-N-n.butylpropionamide.

20. Trans-5(10→9)abeo-6-methyl-ergoline-8β-N-diethyl-propionamide.

21. Trans-5(10→9)abeo-6-methyl-ergoline-8β-N-i.propylpropionamide.

22. Trans-5(10→9)abeo-6-methyl-ergoline-8β-N-methylbutylpropionamide.

23. A process for preparing a compound of the formula (I) as defined in claim 1, said process comprising condensing a 5(10→9)abeo-9,10-didehydro-6-methyl-ergoline-8β-methanol tosylate of the formula (II):

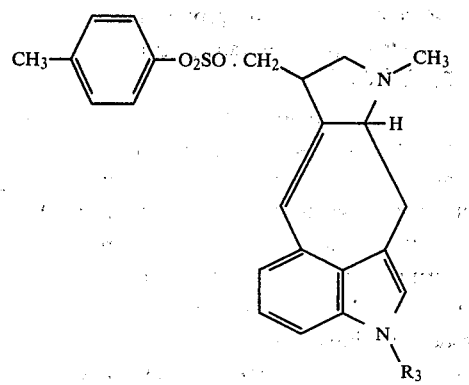

wherein $R_3$ is as defined in claim 1, with a compound of the formula $CH_2R_2.COOC_2H_5$ wherein $R_2$ is as defined in claim 1, the condensation being effected in a polar aprotic solvent at a temperature of from 50° C. to 100° C. for 2 to 10 hours, to obtain a compound of formula (III):

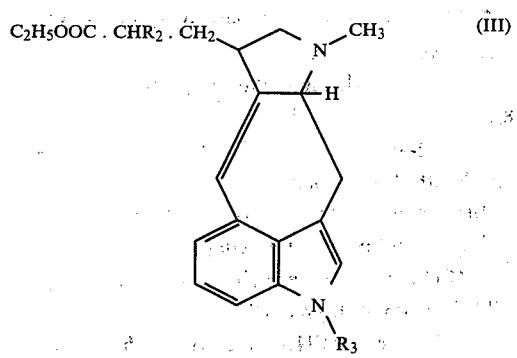

wherein $R_2$ and $R_3$ are as above defined, and (a) isolating the resultant compound, or (b) hydrolysing compound (III) to prepare compound (I) in which $R_1$ represents a carboxy group, or (c) hydrolysing and esterifying compound (III) with an alkanol other than ethanol to prepare compound (I) in which $R_1$ represents an alkoxycarbonyl group other than ethoxycarbonyl, or (d) treating compound (III) with ammonia, benzylamine, piperidine, pyrrolidine, morpholine, an alkylamine or a dialkylamine in which the, or each, alkyl group has from 1 to 4 carbon atoms to prepare compound (I) in which $R_1$ represents a carbamoyl, benzylcarbamoyl, piperidinocarbonyl, 1-pyrrolidinylcarbonyl or morpholinocarbonyl group, or an alkylcarbamoyl or dialkylcarbamoyl group in which the, or each, alkyl group has from 1 to 4 carbon atoms, or (e) hydrolysing and decarboxylating compound (III) in which $R_2$ is cyano to give a propionitrile which, by esterification and treatment with benzylamine, piperidine, pyrrolidine or morpholine, or an alkylamine or dialkylamine in which the, or each, alkyl group has from 1 to 4 carbon atoms, may be converted into compound (I) in which $R_2$ is a hydrogen atom and $R_1$ represents a benzylcarbamoyl, piperidinocarbonyl, 1-pyrrolidinylcarbonyl or morpholinocarbonyl group, or an alkylcarbamoyl or dialkylcarbamoyl group in which the, or each, alkyl group has from 1 to 4 carbon atoms, or (f) catalytically hydrogenating compound (I) prepared according to (a), (b), (c), (d), or (e) to obtain compound (I) wherein ----represents a single bond.

24. A process according to claim 23, in which said polar aprotic solvent is dimethylsulphoxide or dimethylformamide.

* * * * *

UNITED STATES PATENT AND TRADEMARK OFFICE
CERTIFICATE OF CORRECTION

PATENT NO. : 4,317,912         (Page 1 of 2)

DATED : March 2, 1982

INVENTOR(S) : Temperilli et al.

It is certified that error appears in the above—identified patent and that said Letters Patent are hereby corrected as shown below:

In the abstract, 2nd line of the definition for $R_3$ insert -- $\overline{\overline{\phantom{xx}}}$ --.

Column 1, line 31, change "$\underline{\phantom{xx}}$" to -- $\overline{\overline{\phantom{xx}}}$ --.

Column 1, line 38, change "$\underline{\phantom{xx}}$" to -- $\overline{\overline{\phantom{xx}}}$ --.

Column 2, line 5, change "$\underline{\phantom{xx}}$" to -- $\overline{\overline{\phantom{xx}}}$ --.

Column 2, line 37, change "$\underline{\phantom{xx}}$" to -- $\overline{\overline{\phantom{xx}}}$ --.

Column 2, line 39, change "$\underline{\phantom{xx}}$" to -- $\overline{\overline{\phantom{xx}}}$ --.

UNITED STATES PATENT AND TRADEMARK OFFICE
CERTIFICATE OF CORRECTION (Page 2 of 2)

PATENT NO. : 4,317,912
DATED : March 2, 1982
INVENTOR(S) : Temperilli et al.

It is certified that error appears in the above-identified patent and that said Letters Patent are hereby corrected as shown below:

In the reaction scheme shown at the bottom of columns 1 and 2, the upper connecting linkage, please change "$C_2H_5COC.CHR_2.CH_2$" to -- $C_2H_5OOC.CHR_2.CH_2$ --.

In the reaction scheme shown at the bottom of columns 1 and 2, the connecting linkage above the arrow, please change "$CH_2R_2.COOC_2H_6$" to -- $CH_2R_2.COOC_2H_5$ --.

Column 10, Claim 1, 4th line of the definition for $R_3$ change "provisos" to -- proviso --.

Signed and Sealed this

Tenth Day of August 1982

[SEAL]

Attest:

GERALD J. MOSSINGHOFF

Attesting Officer  Commissioner of Patents and Trademarks